United States Patent
Harryson

(10) Patent No.: US 9,701,575 B2
(45) Date of Patent: Jul. 11, 2017

(54) POWDER, METHODS FOR MANUFACTURING AND COMPACTING A POWDER, AND BODIES PRODUCED THEREFROM

(71) Applicant: HARRYSON CONSULTING GMBH, Wilen b. Wollerau (CH)

(72) Inventor: Sigvald Harryson, Malmö (SE)

(73) Assignee: HARRYSON CONSULTING GMBH, Wilen B. Wollerau (CH)

( * ) Notice: Subject to any disclaimer, the term of this patent is extended or adjusted under 35 U.S.C. 154(b) by 0 days.

(21) Appl. No.: 15/030,323

(22) PCT Filed: Oct. 17, 2014

(86) PCT No.: PCT/EP2014/072327
§ 371 (c)(1),
(2) Date: Apr. 18, 2016

(87) PCT Pub. No.: WO2015/055820
PCT Pub. Date: Apr. 23, 2015

(65) Prior Publication Data
US 2016/0257608 A1    Sep. 8, 2016

(30) Foreign Application Priority Data

Oct. 18, 2013    (SE) ........................................ 1351246

(51) Int. Cl.
*C03C 10/04*    (2006.01)
*C03C 10/00*    (2006.01)
(Continued)

(52) U.S. Cl.
CPC ........ *C03C 10/0027* (2013.01); *A61K 6/0008* (2013.01); *A61K 6/024* (2013.01);
(Continued)

(58) Field of Classification Search
CPC .. C03C 10/0009; C03C 10/0027; C03C 10/00
(Continued)

(56) References Cited

U.S. PATENT DOCUMENTS

| | | | |
|---|---|---|---|
| 3,839,001 | A | 10/1974 | Clayton et al. |
| 5,968,856 | A | 10/1999 | Schweiger et al. |

(Continued)

FOREIGN PATENT DOCUMENTS

| | | |
|---|---|---|
| JP | 2000139959 A | 5/2000 |
| WO | WO-2013053865 A2 | 4/2013 |

OTHER PUBLICATIONS

Holand et al., "Principles and Phenomena of Bioengineering with Glass—Ceramics for Dental Restoration", Journal of the European Ceramic Society, Elsevier Science Publishers, Barking, Essex, GB, vol. 27, Issue 23, pp. 1521-1526, Nov. 19, 2006.

(Continued)

*Primary Examiner* — Noah Wiese
(74) *Attorney, Agent, or Firm* — Moser Taboada

(57) ABSTRACT

The present invention relates to a glass ceramic powder comprising i) a glass material formed from a glass mixture containing a lithium and oxygen containing compound selected from $Li_2O$ and/or $Li_2CO_3$, $SiO_2$, $K_2O$, $La_2O_3$, and ii) seed particles comprising $Li_2SiO_3$ crystals and/or $Li_2Si_2O_5$ crystals. The present invention also relates to a method of manufacturing of said glass ceramic powder, a method for preparing compacted and sintered bodies from the glass ceramic powder and bodies obtainable by said method.

16 Claims, 1 Drawing Sheet

(51) Int. Cl.
*A61K 6/027* (2006.01)
*C03C 3/095* (2006.01)
*C03C 4/00* (2006.01)
*C03B 32/02* (2006.01)
*C03B 37/05* (2006.01)
*C03B 19/06* (2006.01)
*C03B 19/10* (2006.01)
*A61K 6/00* (2006.01)
*A61K 6/02* (2006.01)
*C03C 1/02* (2006.01)

(52) U.S. Cl.
CPC ............ *A61K 6/025* (2013.01); *A61K 6/0273* (2013.01); *C03B 19/063* (2013.01); *C03B 19/1045* (2013.01); *C03B 32/02* (2013.01); *C03B 37/055* (2013.01); *C03C 1/026* (2013.01); *C03C 3/095* (2013.01); *C03C 4/0021* (2013.01); *C03C 10/00* (2013.01); *C03C 2204/00* (2013.01)

(58) Field of Classification Search
USPC .............................................. 501/2, 5, 6, 7
See application file for complete search history.

(56) References Cited

U.S. PATENT DOCUMENTS

| | | | |
|---|---|---|---|
| 6,514,893 B1* | 2/2003 | Schweiger | C03C 10/0009 501/5 |
| 6,517,623 B1* | 2/2003 | Brodkin | C03B 19/06 106/35 |
| 2003/0196456 A1* | 10/2003 | Linhart | C03B 32/02 65/33.1 |
| 2012/0308837 A1* | 12/2012 | Schlechtriemen | B28B 1/001 428/446 |
| 2014/0223965 A1* | 8/2014 | Ritzberger | C03C 3/076 65/102 |

OTHER PUBLICATIONS

International Search Report and Written Opinion mailed Jan. 20, 2015 for PCT Application No. PCT/EP2014/072327.

* cited by examiner

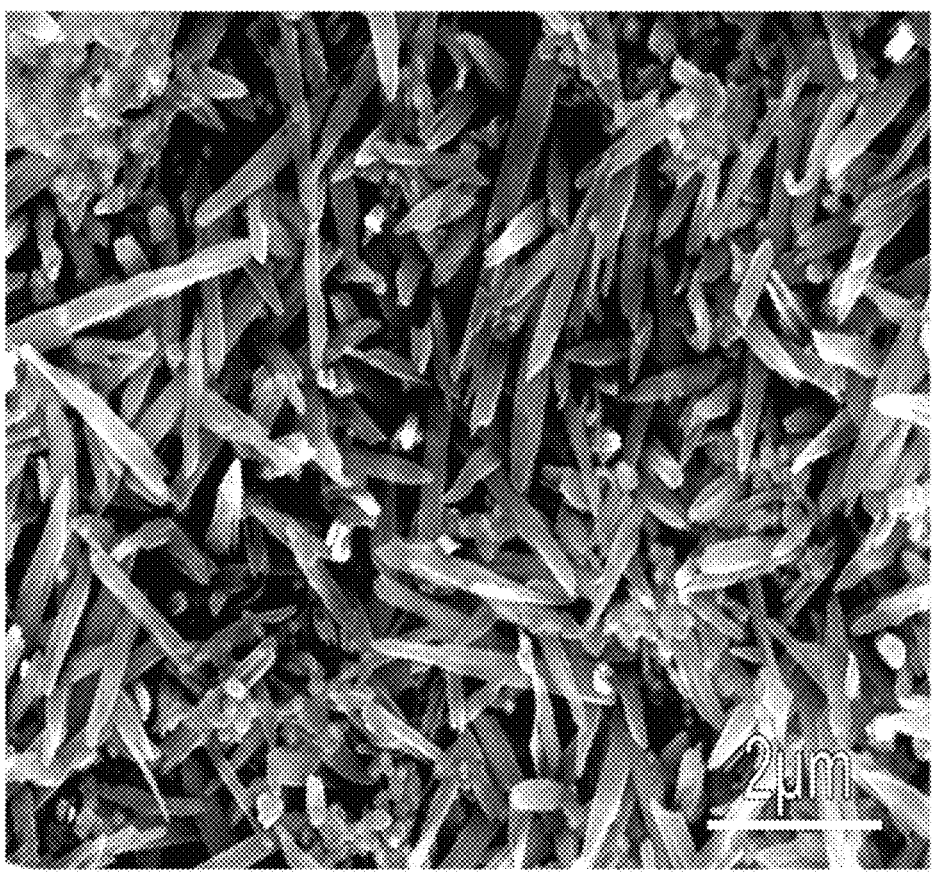

POWDER, METHODS FOR MANUFACTURING AND COMPACTING A POWDER, AND BODIES PRODUCED THEREFROM

TECHNICAL FIELD

The present invention relates to a glass ceramic powder and a method for manufacturing of such a glass ceramic powder. The invention further relates to a method for preparing compacted and sintered bodies from a glass ceramic powder, and the bodies produced.

BACKGROUND

Ceramic- and glass ceramic materials are used as dental materials due to their mechanical properties and aesthetics. The all-ceramic materials, such as zirconia and alumina, have the advantage of high mechanical properties, but are opaque and thus less aesthetically pleasing and more difficult to adapt to the colour of the surrounding teeth than glass ceramic materials such as lithium disilicates ($Li_2Si_2O_5$), which are translucent. However, the glass ceramic materials generally have a fracture toughness and flexural strength considerably lower than the all-ceramic materials do. A translucent material with improved mechanical properties is desirable for dental restoration applications.

Lithium disilicate glass ceramic materials have appealing optical properties in the finally prepared restoration, such as translucence and shade, which imitate the appearance of the natural teeth. They further show high strength and chemical durability so that they can take over the function of the natural tooth material and maintain these properties over a sufficient period of time while being permanently in contact with fluids in the oral cavity. It is also desirable to machine them in an easy manner into the desired shape without undue wear of the tools and within short times.

US2009/0042714 discloses lithium silicate materials for use in dental products.

There is an increasing demand for new methods of producing crack-free samples with desirable mechanical properties and attractive appearance resembling natural teeth, having large sizes suitable for large dental works such as bridges, for example samples larger than 1 cm$^3$.

SUMMARY

Purposes of the present invention include providing solutions to problems identified with regard to prior art. Shaping of a restoration to the desired geometry is benefited from a relatively low strength of the material and is therefore in contrast to the desired properties mentioned above for a final restoration. It is possible to achieve both benefits through processing in two steps. With the present invention materials with improved mechanical properties and tailored microstructure are obtained. The use of a seed material contributes to the growth of elongated crystals. Further, fine grain materials can be used without blackening during the processing into bodies.

The present invention allow for efficient manufacturing of glass ceramic materials suitable for, e.g. dental applications.

According to a first aspect of the present invention there is provided a glass ceramic powder comprising
i) a glass material formed from a glass mixture containing
   a lithium and oxygen containing compound selected from $Li_2O$ and/or $Li_2CO_3$
   $SiO_2$
   $K_2O$
   $La_2O_3$
and
ii) seed particles comprising $Li_2SiO_3$ crystals and/or $Li_2Si_2O_5$ crystals.

According to one embodiment the glass mixture may further comprise at least one compound selected from $ZrO_2$, $CeO_2$, $P_2O_5$, $Al_2O_3$, Zr, C, and compounds of the elements Pt, Ag, Cu and W.

According to one embodiment the average particle size of the glass ceramic powder is in the range of 0.25 to 7 μm, preferably 1-5 μm, preferably 2-4 μm.

According to one embodiment the ratios in the glass mixture may be
   2-17 wt % of lithium and oxygen containing compound selected from $Li_2O$ and/or $Li_2CO_3$
   70-77 wt % of $SiO_2$
   2-4 wt % of $K_2O$
   3-5 wt % of $La_2O_3$
wherein the sum of the percentages is not to exceed 100 wt %.

According to one embodiment the ratios in the glass mixture may be
   2.9-15.8 wt % of lithium and oxygen containing compound selected from $Li_2O$ and/or $Li_2CO_3$
   71.6-75.9 wt % of $SiO_2$
   3.0-3.5 wt % of $K_2O$
   3.3-4.8 wt % of $La_2O_3$
wherein the sum of the percentages is not to exceed 100 wt %.

According to one embodiment the seed particles may be in an amount of 1-6 wt % based on the weight of the glass material.

According to a second aspect of the present invention there is provided a method of manufacturing of a glass ceramic powder, the method comprising the steps of:
I) providing a glass material, wherein said glass material is prepared by
   a) providing a glass mixture comprising
      a lithium and oxygen containing compound selected from $Li_2O$ and/or $Li_2CO_3$,
      $SiO_2$,
      $K_2O$, and
      $La_2O_3$
   b) heating the glass mixture such that the mixture melts,
   c) cooling the melted glass mixture by contacting it with water, whereby forming a solid frit, and
   d) pulverizing the solid frit into a glass material powder;
II) providing a seed material, wherein said seed material is prepared by
   e) providing a seed mixture of
      a lithium and oxygen containing compound selected from $Li_2O$ and/or $Li_2CO_3$, and
      $SiO_2$
   f) heating the seed mixture in at least one step such that the seed mixture melts and reacts, whereby lithium metasilicate crystals and/or lithium disilicate crystals are formed,
   g) pulverizing the formed crystals into a seed powder; and
III) mixing said glass material powder with said seed powder.

According to one embodiment said heating of the glass mixture is performed at a temperature of 1250-1550° C., preferably 1300-1500° C.

According to one embodiment said heating of the glass mixture is performed during a time period of 1-3 hours, preferably 1.5-2.5 hours.

According to one embodiment said heating of the seed mixture is performed at a temperature of 750-900° C., preferably 800-850° C.

According to one embodiment the seed has a molar ratio of the $SiO_2$ to the lithium and oxygen containing compound of 2:1 to 1:1.

According to one embodiment said lithium metasilicate crystals and/or lithium disilicate crystals of the seed mixture may have a length of 1-5 µm, preferably 2-3 µm.

According to one embodiment the mixing of said glass material powder with said seed powder may be performed in an alcohol.

According to one embodiment the mixing of said glass material powder with said seed powder may be performed in a pulverizing unit, preferably a mill or a grinder, preferably a ball mill.

According to one embodiment the mixing of said glass material powder with said seed powder in an alcohol may be followed by evaporation of said alcohol.

According to a third aspect of the present invention there is provided a method for preparing compacted and sintered bodies from a glass ceramic powder according to the first aspect, the method comprising:
providing said glass ceramic powder,
compacting the glass ceramic powder into a green body,
sintering the green body,
hot pressing the sintered green body.

According to one embodiment the compacting may be an uniaxial pressing.

According to one embodiment the sintering may be selected from the group comprising vacuum sintering and nitrogen sintering, or combinations thereof.

According to one embodiment the method for preparing compacted and sintered bodies further comprises machining of the sintered and hot pressed body by cutting, grinding, trimming, milling or polishing, or combinations thereof, thereby changing the shape of said body.

According to one embodiment the step of sintering and/or hot pressing may be performed at temperatures in the range of 750-950° C.

According to one embodiment the step of hot pressing may be performed using a pressure of about 10 to 30 MPa, preferably 15-25 MPa.

According to one embodiment the method for preparing compacted and sintered bodies may be for manufacturing of a dental product for dental restoration.

According to a forth aspect of the present invention there is provided a body obtainable by the process according to the third aspect.

According to one embodiment the body may have a density of 2.4-2.6 g/cm$^3$.

According to one embodiment the body may have a fracture toughness of at least 3.0 MPa-m$^{1/2}$; and/or a flexural strength of at least 360 MPa.

According to one embodiment the body may comprise lithium disilicate crystals having a length of 5 micrometers or more, such as 10 micrometers or more, as seen along one or more axes.

According to one embodiment, the body may comprise lithium disilicate crystals having a length of 2 micrometers or more, such as 2-3 micrometers. The width of the lithium disilicate crystals may be, for example, 0.4-0.5 micrometers.

Embodiments and discussions with regard to one aspect may be relevant to one or more other aspect(s). For example, the first aspect may also be relevant with regard to the second, third, and fourth aspects. References to these embodiments are hereby made, where relevant.

DESCRIPTION OF FIGURE

The FIGURE illustrates sintered material according to an embodiment.

DETAILED DESCRIPTION

It has surprisingly been found that by using a glass mixture with seed particles as starting material it has become possible to provide a glass ceramic mixture which has lithium disilicate crystals ($Li_2Si_2O_5$) as main crystalline phase in a processed body. The crystalline phase makes the obtained material suitable for dental restorations due to its good chemical durability, appealing optical properties, good flexural strength and fracture toughness.

Compared to known methods the use of the seed material according to the present invention a higher degree of crystallization, as well as an increased size and better structural alignment of the lithium metasilicate crystals is obtained. These features are obtained using the seed material disclosed herein and the two-step synthesis process with introduction of the seed material. The introduction of the seed material makes it possible to omit the step of nucleation and at the same time gain a better control over the crystallization process. Further processing via sintering and hot pressing allows the use of very fine particles in the powders processed, leading to improved density and strength of the resulting material. A controlled crystallization process via seed introduction allows active growth of elongated needle-shaped crystals uniformly distributed across the formed glass ceramic body, which results in excellent mechanical properties.

It is provided a glass ceramic powder comprising a glass material and seed particles comprising $Li_2SiO_3$ crystals. The glass material is formed from a glass mixture containing a lithium and oxygen containing compound selected from $Li_2O$ and/or $Li_2CO_3$, $SiO_2$, $K_2O$ and $La_2O_3$. The glass mixture may comprise further components such as at least one compound selected from $ZrO_2$, $CeO_2$, $P_2O_5$, $Al_2O_3$, Zr, C, and compounds of the elements Pt, Ag, Cu and W; preferably at least one compound selected from $ZrO_2$, $CeO_2$, $P_2O_5$, $Al_2O_3$, Zr, and C; such as at least one compound selected from $ZrO_2$, $CeO_2$, $P_2O_5$, $Al_2O_3$. The ratios of the components in the glass mixture are about 2-17 wt % of lithium and oxygen containing compound selected from $Li_2O$ and/or $Li_2CO_3$; 70-77 wt % of $SiO_2$; 2-4 wt % of $K_2O$; and 3-5 wt % of $La_2O_3$. However, the sum of the components' percentages is not to exceed 100 mol %. Even if more components are included, the four components mentioned above are within said ranges. In another embodiment the ratios are 2.9-15.8 wt % of lithium and oxygen containing compound selected from $Li_2O$ and/or $Li_2CO_3$; 71.6-75.9 wt % of $SiO_2$; 3.0-3.5 wt % of $K_2O$; and 3.3-4.8 wt % of $La_2O_3$.

The seed particles comprising $Li_2SiO_3$ crystals and/or $Li_2Si_2O_5$ are prepared from $Li_2O$ and/or $Li_2CO_3$, and $SiO_2$. The seed particles may be added in an amount of 1-6 wt % based on the weight of the glass material, e.g. 2-5 wt %, or about 3-4 wt %. The seed particles may have an average particle size within the range of 0.25 to 7 µm, e.g. 1-5 µm or 2-4 µm. The seed crystals are elongated needle shaped crystals. The seed crystals may have a length of 1-4 µm, for example, 2-3 µm. The width of the seed crystals may be 0.25 to 0.75 µm, for example, 0.4-0.6 µm.

The average particle size of the glass ceramic powder is preferably within the range of 0.25 to 7 µm, e.g. 1-5 µm or 2-4 µm. Such small particle sizes would upon formation of sintered bodies using conventional techniques show problems with darkening of the final product because of blackening of the fine grain material. This problem is however solved with the combination of sintering and hot pressing according to the present method.

The preparation of the glass ceramic powder comprises the steps of:
I) providing a glass material, wherein said glass material is prepared by
   a) providing a glass mixture comprising a lithium and oxygen containing compound selected from $Li_2O$ and/or $Li_2CO_3$, $SiO_2$, $K_2O$, and $La_2O_3$;
   b) heating the glass mixture such that the mixture melts;
   c) cooling the melted glass mixture by contacting it with water, whereby forming a solid frit; and
   d) pulverizing the solid frit into a glass material powder;
II) providing a seed material, wherein said seed material is prepared by
   e) providing a seed mixture of a lithium and oxygen containing compound selected from $Li_2O$ and/or $Li_2CO_3$, and $SiO_2$;
   f) heating the seed mixture such that the seed mixture melts and reacts, whereby lithium metasilicate crystals ($Li_2SiO_3$) are formed;
   g) pulverizing the formed crystals into a seed powder; and
III) mixing said glass material powder with said seed powder and thereby forming said glass ceramic powder.

The glass mixture is preferably heated to a temperature of 1250-1550° C., e.g. 1300-1500° C. for the glass mixture to melt. The heating of the glass mixture may be performed for a time period of 1-3 hours, e.g. 1.5-2.5 hours. During heating the mixture may be mixed. Mixing may be performed continuously or intermittently. The material of the agitator performing the mixing may influence the ratio of mixing and non-mixing of the material. Aluminium may react with the glass melt thus stirring may not be performed for too long. An agitator made of silica or platinum is better. As an example stirring may occur for 5 minutes about every half an hour, e.g. 5 minutes stirring, 25 minutes without stirring etc, or 5 minutes about every 15 minutes.

After the step d) the glass material powder may be subjected to a heating step. Such a heating step may be performed at a temperature in the range of 450-550° C., preferably 480-500° C.

During the glass material powder production process, lithium metasilicate crystals are formed. Thus, the glass mixture formed partly comprises $Li_2SiO_3$.

The seed mixture is preferably heated to a temperature of 750-900° C., e.g. 800-850° C. for the seed mixture to melt. The heating of the seed mixture may take place as one step or as multiple steps, e.g. a two step process. If a two step process is performed e.g. lithium metasilicate crystals may be formed in a first step and further heating may provide lithium disilicate crystals. During heating the mixture may be mixed. Mixing may be performed continuously or intermittently. The material of the agitator performing the mixing may influence the ratio of mixing and non-mixing of the material. As an example stirring may occur for 5 minutes about every half an hour, e.g. 5 minutes stirring, 25 minutes without stirring etc, or 5 minutes about every 15 minutes. The seed mixture may have a molar ratio of the $SiO_2$ to the lithium and oxygen containing compound of at most 2, preferably 1:1. Thus, for example, the seed mixture may have a molar ratio of ($SiO_2$):(lithium and oxygen containing compound) of 2:1 to 1:1. During the processing of the seed mixture lithium metasilicate crystals and/or lithium disilicate crystals formed may have a length of 1-5 μm, preferably 2-3 μm. After the formation of a crystal containing seed material, the material is pulverized, e.g. using a ball mill, forming a seed powder.

Formed glass material powder and seed powder are mixed with each other. This may be done in a suitable medium such as an alcohol. Mixing is preferably performed in a pulverizing unit, e.g. a mill or a grinder. The mill may be a ball mill. After the mixing the medium is preferably evaporated from the formed powder mixture forming a glass ceramic powder that may be further processed into bodies for use within dentistry.

Bodies formed from said glass ceramic powder may be provided by the production method comprising provision of said glass ceramic powder; compaction of the glass ceramic powder into a green body; sintering the green body; hot pressing the sintered green body. The production method may further include a step of machining the sintered and hot pressed body by cutting, grinding, trimming, milling or polishing, or combinations thereof, thereby changing the shape of said body. Cutting may be done with diamond thread. The compacting step may be an uniaxial pressing. Said machining may be performed between the sintering and the hot pressing steps, or may be performed after the hot pressing step. Further, the sintering may be selected from the group comprising vacuum sintering, nitrogen sintering, or combinations thereof. Preferably, the sintering may occur at a temperature in the range of 750-950° C. The hot pressing step may occur at a temperature in the range of 750-950° C. The pressure during the hot pressing step may be about 10 to 30 MPa, e.g. 15-25 MPa.

The above production method may be used for manufacturing of dental products for dental restoration. The body obtainable according to the above production method may have a density of 2.4-2.6 g/cm$^3$. The formed body may comprise lithium disilicate crystals having a length of 5 micrometers or more, such as 10 micrometers or more, as seen along one or more axes.

The glass ceramic powder manufactured as disclosed above comprises toughened lithium metasilicate glass ceramics particularly suitable for example for the manufacturing of bodies or blocks for full anatomic dental restorations. Such bodies or blocks may be fabricated with CAD/CAM process into a suitable shape. The material obtained is characterized by higher toughness in comparison with prior art, which allows using it also for large posterior dental restorations, such as bridges. The glass material comprising $Li_2O$, $SiO_2$, $K_2O$ and $La_2O_3$ is an efficient material for obtaining a toughened glass ceramic material.

Properties of bodies manufactured from glass ceramic powders manufactured as disclosed above may be characterized by having properties selected from, e.g: a fracture toughness of at least 3.0 MPa-m$^{1/2}$, e.g. 3.4 MPa-m$^{1/2}$ or above; a flexural strength of at least 360 MPa, e.g. 380 MPa; a considerable part of the matter in the form of crystals having a length of 5 micrometers or more along at least one axis; a density of 2.4-2.6 g/cm$^3$, such as for example 2.5 g/cm$^3$; and a translucency of the material of 70% or more. Such bodies with such properties have shown to be particularly suitable for dental repairs.

The compacted and sintered body may efficiently be manufactured in wide range of sizes. For example, a body may have a size suitable for a dental crown while another body may have a size suitable for a dental full-arch restoration. Another body may be suitable for manufacturing of multiple restorations out of one piece, thus minimizing waste material and tool changing.

The sintering may result in crystallisation and formation of lithium disilicate glass ceramics. The sintering may cause a transport of ions between particles of the powder and may be for example reactive sintering increasing the toughness of the sintered body. The sintering may result in solidification of the glass ceramic. The reactive sintering may efficiently result in the formation of crystals in the glass ceramic, the crystal having a length of 5 micrometers or more, such as 10 micrometers or more, as seen along one or more axes.

The sintered and heat pressed body may, thus, be selected to have a shape of, for example, a tooth, a crown, or a bridge, or any other suitable shape for dental repair or restoration purposes. The shape may be selected in accordance with a dental restoration plan.

The machining may be controlled by a computer, preferably a computer using CAD/CAM-based milling devices.

It will be appreciated that numerous variants of the embodiments described above are possible within the scope of the appended claims.

EXAMPLE

A glass material and seed particles comprising elongated needle shaped lithium disilicate crystals of 0.5 micrometers width and 2-3 micrometers length were prepared and used in experiments.

Preparation of the Glass Material:

A glass mixture according to table 1 was mixed and melted at a temperature of 1450° C. for 2 hours. Stirring was made for 20 minutes in total over these 2 hours while the temperature was maintained at 1450° C. according to the following scheme: The stirring was done 4 times over the 2 hours, and the duration of each stirring session was 5 minutes, with breaks in between the stirring sessions of 10 minutes. Thereafter, the thus obtained glass melt, was poured into water for quenching. The thus obtained glass frit was pulverized by milling in a ball mill, for approximately 10 hours, until the particles reached 3 micrometer on average.

TABLE 1

| Glass mixture: | | | |
|---|---|---|---|
| $Li_2O$ | $SiO_2$ | $K_2O$ | $La_2O_3$ |
| wt. % 15.8 | 75.9 | 3.47 | 4.81 |

Preparation of the Seed Material:

Lithium carbonate and silica were mixed and heated to 800-850° C. and reached crystallization during forming of lithium metasilicate ($Li_2SiO_3$) and of lithium-disilicate ($Li_2Si_2O_5$) in a two-step process described by reactions (i) and (ii), wherein lithium metasilicate is formed according to (i) and lithium disilicate is formed according to (ii).

$Li_2CO_3 + SiO_2 \rightarrow Li_2SiO_3$ (i)

$Li_2SiO_3 + SiO_2 \rightarrow Li_2Si_2O_5$ (ii)

The proportion based on mol between lithium metasilicate and lithium disilicate was 1:1. Thereafter, wet ball milling with alcohol provided the seed material.

Preparation of Compacted and Sintered Bodies:

The glass material powder and the seed material were mixed followed by uniaxial pressing to form a green body. Thereafter, vacuum sintering and hot pressing (20 MPa 850° C. for 30 minutes) were performed. Thereafter, the sintered body was cut followed by grinding and polishing. Dimensions of the thus obtained samples were approximately 4×3×23 mm³.

Results:

The sintered bodies were validated according to the following:

Flexural strength, of (MPa), Average±standard deviation: 325±9

Fracture toughness $K_{1c}$ (MPa*m$^{0.5}$), load 1000 g, average±standard deviation: 2.42±0.24.

A fracture toughness $K_{1c}$ (MPa*m$^{0.5}$) of 2.93 was obtained for a sample.

The flexural strength was obtained according to a 3-point bending test described by $$\sigma_f = \frac{3Fa}{bd^2},$$

where $\sigma_f$ is flexural strength (MPa), F is load at fracture (N), a is the length of the fixture moment arm (mm), b is the width of the specimen (mm), and d is the thickness of the specimen (mm).

The fracture toughness was obtained according to $$K_{1c} = 0.0319 * \frac{P}{al^{0.5}},$$

where P is the applied load, c is the crack length from the center of the indenter, a is half of the length of the indenter diagonal and I is the length of the crack measured from the corner of the indenter.

The FIGURE illustrates a sintered body described according to the example with high degree of crystallization and comprising lithium disilicate crystals having a length of approximately 2-3 micrometers and a width of approximately 0.4-0.5 micrometers.

According to one embodiment the body may have a fracture toughness of at least 2.4 MPa*m$^{1/2}$, such as 2.9 MPa*m$^{1/2}$; and/or a flexural strength of at least 325 MPa; and/or comprising lithium disilicate crystals having a length of 2 micrometers or more, such as 2-3 micrometers.

While the invention has been described with reference to a number of preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A glass ceramic powder comprising
   i) a glass material formed from a glass mixture containing
      a lithium and oxygen containing compound selected from $Li_2O$ and/or $Li_2CO_3$
      $SiO_2$
      $K_2O$
      $La_2O_3$; and ii) seed particles comprising $Li_2SiO_3$ crystals and/or $Li_2Si_2O_5$ crystals,
wherein the seed particles is in an amount of 1-6 wt % based on the weight of the glass material.

2. The powder according to claim 1, wherein the glass mixture further comprising at least one compound selected from $ZrO_2$, $CeO_2$, $P_2O_5$, $Al_2O_3$, Zr, C, and compounds of the elements Pt, Ag, Cu and W.

3. The powder according to claim 1, wherein the average particle size of the glass ceramic powder is in the range of 0.25 to 7 µm, 1-5 µm, or 2-4 µm.

4. The powder according to claim 1, wherein the ratios in the glass mixture are
2-17 wt % of lithium and oxygen containing compound selected from $Li_2O$ and/or $Li_2CO_3$
70-77 wt % of $SiO_2$
2-4 wt % of $K_2O$
3-5 wt % of $La_2O_3$
wherein the sum of the percentages is not to exceed 100 wt %.

5. A method of manufacturing a glass ceramic powder, the method comprising the steps of:
I) providing a glass material, wherein said glass material is prepared by
a) providing a glass mixture comprising
a lithium and oxygen containing compound selected from $Li_2O$ and/or $Li_2CO_3$,
$SiO_2$,
$K_2O$, and
$La_2O_3$,
b) heating the glass mixture such that the mixture melts,
c) cooling the melted glass mixture by contacting it with water, whereby forming a solid frit, and
d) pulverizing the solid frit into a glass material powder;
II) providing a seed material, wherein said seed material is prepared by
e) providing a seed mixture of
a lithium and oxygen containing compound selected from $Li_2O$ and/or $Li_2CO_3$, and
$SiO_2$,
f) heating the seed mixture in at least one step such that the seed mixture melts and reacts, whereby lithium metasilicate crystals and/or lithium disilicate crystals are formed, and
g) pulverizing the formed crystals into a seed powder; and
III) mixing said glass material powder with said seed powder.

6. The method according to claim 5, wherein said heating of the glass mixture is performed at a temperature of 1250-1550° C., or 1300-1500° C.

7. The method according to claim 5, wherein said heating of the glass mixture is performed during a time period of 1-3 hours, or 1.5-2.5 hours.

8. The method according to claim 5, wherein said heating of the seed mixture is performed at a temperature of 750-900° C., or 800-850° C.

9. The method according to claim 5, wherein the seed has a molar ratio of the $SiO_2$ to the lithium and oxygen containing compound of 2:1 to 1:1.

10. The method according to claim 5, wherein said lithium metasilicate crystals and/or lithium disilicate crystals of the seed mixture have a length of 1-5 µm, or 2-3 µm.

11. A method for preparing compacted and sintered bodies from a glass ceramic powder according to claim 1, the method comprising:
providing said glass ceramic powder;
compacting the glass ceramic powder into a green body;
sintering the green body; and
hot pressing the sintered green body,
wherein the sintering is selected from the group comprising vacuum sintering and nitrogen sintering, or combinations thereof.

12. The method according to claim 11, wherein the compacting is an uniaxial pressing.

13. The method according to claim 11, further comprising machining of the sintered and hot pressed body by cutting, grinding, trimming, milling or polishing, or combinations thereof, thereby changing the shape of said body.

14. The method according to claim 11, wherein the step of sintering and/or hot pressing are performed at temperatures in the range of 750-950° C.

15. The method according to claim 11, wherein the step of hot pressing is performed using a pressure of about 10 to 30 MPa, or 15-25 MPa.

16. The method according to claim 11, for manufacturing of a dental product for dental restoration.

* * * * *